United States Patent
Ohtaki et al.

(10) Patent No.: US 7,307,160 B1
(45) Date of Patent: Dec. 11, 2007

(54) OTSA GENE ENCODING TREHALOSE-6-PHOSPHATE SYNTHASE FROM A CORYNEFORM BACTERIUM

(75) Inventors: Hiromi Ohtaki, Kawasaki (JP); Jun Nakamura, Kawasaki (JP); Hiroshi Izui, Kawasaki (JP); Tsuyoshi Nakamatsu, Kawasaki (JP)

(73) Assignee: Ajinomoto Co. Inc., Tokyo (JP)

( * ) Notice: Subject to any disclaimer, the term of this patent is extended or adjusted under 35 U.S.C. 154(b) by 444 days.

(21) Appl. No.: 10/637,551

(22) Filed: Aug. 11, 2003

Related U.S. Application Data

(62) Division of application No. 09/895,382, filed on Jul. 2, 2001, now abandoned.

(30) Foreign Application Priority Data

Jul. 5, 2000 (JP) ............................. 2000-204256

(51) Int. Cl.
C07H 21/04 (2006.01)
A61K 38/00 (2006.01)
C12N 1/20 (2006.01)

(52) U.S. Cl. ................. 536/23.2; 530/333; 435/252.32
(58) Field of Classification Search ...................... None
See application file for complete search history.

(56) References Cited

U.S. PATENT DOCUMENTS

2002/0192674 A1   12/2002   Hermann et al.
2002/0197605 A1*  12/2002   Nakagawa et al. ............ 435/6

FOREIGN PATENT DOCUMENTS

| EP | 0 771 879 | 5/1997 |
|---|---|---|
| EP | 1 103 611 | 5/2001 |
| FR | 2 747 131 | 10/1997 |
| JP | 5-276935 | 10/1993 |
| KR | 0165836 | 1/1999 |
| WO | 01/00843 | 1/2001 |
| WO | 02/051231 A1 | 7/2002 |

OTHER PUBLICATIONS

Bonini et al. (2000), Biochem J., vol. 350, pp. 261-268.*

S. T. Cole, et al., Genbank Accession Z95390, "Deciphering the Biology of *Mycobacterium tuberculosis*/From the Complete Genome Sequence" 1998. NCB1 Report Only No copy of Nature.

K.A.L. DeSmet, et al., Microbiology, vol. 146, No. 1, pp. 199-208, "Three Pathways for Trehalose Biosynthesis In Mycobacteria", 2000.

H.M. Giaever, et al., Journal of Bacteriology, vol. 170, No. 6, pp. 2841-2849, "Biochemical and Genetic Characterization of Osmoregulatory Trehalose Synthesis In *Escherichia coli*", Jun. 1988.

I. Kaasen, et al., Gene, vol. 145, No. 1, pp. 9-15, "Analysis of the otsBA Operon for Osmoregulatory Threhalose Synthesis in *Escherichia coli* and Homology of the OtsA and OtsB Proteins to the Yeast Trehalose-6-Phosphate Synthase/Phosphatase Complex", 1994.

Y.H. Kim, et al., AF 039919, "Trehalose Synthesis by Sequential Reactions of Recombinant Maltooligosyltrehalose Synthase and MalTooligosyltrehalose Trehalohydrolase From *Brevibacterium helvolum*", 2000. No Copy of Journal, Gene Acc NCBI Report only.

K. Maruta, et al., Biochemica et Biophysica Acta, vol. 1289, No. 1, pp. 10-13, "Cloning and Sequencing of Trehalose Bisynthesis Genes From *Arthrobacter* SP. Q36", 1996.

K. Maruta, et al., Biosci. Biotech. Biochem., vol. 60, No. 4, pp. 717-720, "Cloning and Sequencing of Trehalose Biosynthesis Genes From *Rhizobium* SP. M-11", 1996.

Gourdon et al., Metabolic Analysis of Glutamate Production by *Corynebacterium glutamicum*. Metabolic Engineering (Jul. 1999) 1:224-231.

R. Kraemer, Journal of Biotechnology, vol. 45 No. 1, pp. 1-21 "Genetic and Physiological Approaches For The Production OPf Amino Acids", 1996.

* cited by examiner

*Primary Examiner*—Kathleen Bragdon
*Assistant Examiner*—Alexander Kim
(74) *Attorney, Agent, or Firm*—The Nath Law Group; Gary M. Nath; Susanne M. Hopkins

(57) ABSTRACT

L-Glutamic acid is produced by culturing a coryneform bacterium having L-glutamic acid producing ability, in which trehalose synthesis ability is decreased or deleted by, for example, disrupting the otsA gene derived from a coryneform bacterium source, coding for trehalose-6-phosphate synthase, to produce and accumulate L-glutamic acid in the medium, and collecting the L-glutamic acid from the medium.

4 Claims, No Drawings

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer for
      PCR
<220> FEATURE:
<221> NAME/KEY: misc_feature
<222> LOCATION: (3,9,18)
<223> OTHER INFORMATION: n = a or g or c or t

<400> SEQUENCE: 1
canathggnt tyttyytnca                                            20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: primer for
      PCR
<220> FEATURE:
<221> NAME/KEY: misc_feature
<222> LOCATION: (3,11,19)
<223> OTHER INFORMATION: n = a or g or c or t

<400> SEQUENCE: 2
canarrttca tnccrtcnc                                             19

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: primer for
      PCR

<400> SEQUENCE: 3
gaatcatcca tataagatcc ggc                                        23
```

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 4
tagctttgta gttgttgcta accg                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 5
agcgaacttg aggtttactt cccg                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 6
tgctggttcc tggcattttg cgcc                                          24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 7
tcgaacaatc tcttcacgcc                                               20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 8
gaatcccacc aaatctgcgc c                                             21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 9
tgatgttgaa atgtttgggg                                               20
```

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 10
gatgtcatgc tggttacgcc                                             20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: primer for
      PCR

<400> SEQUENCE: 11
caaagcacca gtgccgtcgc gg                                          22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 12
tgttcgtttt cattcgcgtt gccg                                        24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 13
atagtttcct ggattgtttg gcgc                                        24

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: primer for
      PCR
<220> FEATURE:
<221> NAME/KEY: misc_feature
<222> LOCATION: (9)
<223> OTHER INFORMATION: n = a or g or c or t

<400> SEQUENCE: 14
caraayccnt ggtggtgg                                               18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: primer for
      PCR
<220> FEATURE:
<221> NAME/KEY: misc_feature
```

<222> LOCATION: (3,6,15)
<223> OTHER INFORMATION: n = a or g or c or t

<400> SEQUENCE: 15
ggncgncgrt trtcnggrtc                                            20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 16
cgagctcttc attgatggcg                                            20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 17
gcagctacac acgagttggg                                            20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 18
gcaacaccta aatggttggg                                            20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 19
gcaagaagtc tacaagcgcc                                            20

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: primer for
      PCR

<400> SEQUENCE: 20
gccaacgtat tcacgg                                                16

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer for

PCR

<400> SEQUENCE: 21
tgatgaacca ctcgatcccc                                           20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 22
aagacaccac cttctaccgc                                           20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 23
caagtggaat tctgcagcgg                                           20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: primer for
      PCR

<400> SEQUENCE: 24
cctcctacaa aacctgctgg g                                         21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 25
tcgcggatag cttttagggc                                           20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 26
tgagttttta gaagactccc                                           20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: primer for
      PCR

<400> SEQUENCE: 27
cgcttcagtg gtgttgtccc                                                20

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: primer for
      PCR

<400> SEQUENCE: 28
cgtaccactc cacggaaatt cccg                                           24

<210> SEQ ID NO 29
<211> LENGTH: 2369
<212> TYPE: DNA
<213> ORGANISM: Brevibacterium lactofermentum
<220> FEATURE:
<221> NAME/KEY: CDS
<222> LOCATION: (484)..(1938)
<223> OTHER INFORMATION:

<400> SEQUENCE: 29

```
acagaatcag cgccggcaga gaaacgtcca aagactaatc agagattcgg tataaaggta     60
aaaatcaacc tgcttaggcg tctttcgctt aaatagcgta gaatatcggg tcgatcgctt    120
ttaaacactc aggaggatcc ttgccggcca aatcacgga cactcgtccc accccagaat    180
cccttcacgc tgttgaagag gaaaccgcag ccggtgcccg caggattgtt gccacctatt    240
ctaaggactt cttcgacggc gtcactttga tgtgcatgct cggcgttgaa cctcagggcc    300
tgcgttacac caaggtcgct tctgaacacg aggaagctca gccaaagaag gctacaaagc    360
ggactcgtaa ggctaccagc taagaaggct gctgctaaga aaacgaccaa gaagaccact    420
aagaaaacta ctaaaaagac caccgcaaag aagaccacaa agaagtctta agccggatct    480
```

| tat atg gat gat tcc aat agc ttt gta gtt gtt gct aac cgt ctg cca | 528 |
|---|---|
|     Met Asp Asp Ser Asn Ser Phe Val Val Val Ala Asn Arg Leu Pro | |
|     1               5               10             15 | |
| gtg gat atg act gtc cac cca gat ggt agc tat agc atc tcc ccc agc | 576 |
| Val Asp Met Thr Val His Pro Asp Gly Ser Tyr Ser Ile Ser Pro Ser | |
|                20               25              30 | |
| ccc ggt ggc ctt gtc acg ggg ctt tcc ccc gtt ctg gaa caa cat cgt | 624 |
| Pro Gly Gly Leu Val Thr Gly Leu Ser Pro Val Leu Glu Gln His Arg | |
|         35                   40                45 | |
| gga tgt tgg gtc gga tgg cct gga act gta gat gtt gca ccc gaa cca | 672 |
| Gly Cys Trp Val Gly Trp Pro Gly Thr Val Asp Val Ala Pro Glu Pro | |
|   50                  55                60 | |
| ttt cga aca gat acg ggt gtt ttg ctg cac cct gtt gtc ctc act gca | 720 |
| Phe Arg Thr Asp Thr Gly Val Leu Leu His Pro Val Val Leu Thr Ala | |
| 65                  70                75 | |
| agt gac tat gaa ggc ttc tac gag ggc ttt tca aac gca acg ctg tgg | 768 |
| Ser Asp Tyr Glu Gly Phe Tyr Glu Gly Phe Ser Asn Ala Thr Leu Trp | |
| 80                  85                90              95 | |
| cct ctt ttc cac gat ctg att gtt act ccg gtg tac aac acc gat tgg | 816 |
| Pro Leu Phe His Asp Leu Ile Val Thr Pro Val Tyr Asn Thr Asp Trp | |
|                   100             105            110 | |
| tgg cat gcg ttt cgg gaa gta aac ctc aag ttc gct gaa gcc gtg agc | 864 |
| Trp His Ala Phe Arg Glu Val Asn Leu Lys Phe Ala Glu Ala Val Ser | |
|              115               120            125 | |
| caa gtg gcg gca cac ggt gcc act gtg tgg gtg cag gac tat cag ctg | 912 |

```
        Gln Val Ala Ala His Gly Ala Thr Val Trp Val Gln Asp Tyr Gln Leu
                    130                 135                 140 ttg ctg gtt cct ggc att ttg cgc cag atg cgc ctt gat ttg aag atc        960
Leu Leu Val Pro Gly Ile Leu Arg Gln Met Arg Leu Asp Leu Lys Ile
            145                 150                 155 ggt ttc ttc ctc cac att ccc ttc cct tcc cct gat ctg ttc cgt cag       1008
Gly Phe Phe Leu His Ile Pro Phe Pro Ser Pro Asp Leu Phe Arg Gln
160                 165                 170                 175 ctg ccg tgg cgt gaa gag att gtt cga ggc atg ctg ggc gca gat ttg       1056
Leu Pro Trp Arg Glu Glu Ile Val Arg Gly Met Leu Gly Ala Asp Leu
                180                 185                 190 gtg gga ttc cat ttg gtt caa aac gca gaa aac ttc ctt gcg tta acc       1104
Val Gly Phe His Leu Val Gln Asn Ala Glu Asn Phe Leu Ala Leu Thr
            195                 200                 205 cag cag gtt gcc ggc act gcc ggg tct cat gtg ggt cag ccg gac acc       1152
Gln Gln Val Ala Gly Thr Ala Gly Ser His Val Gly Gln Pro Asp Thr
        210                 215                 220 ttg cag gtc agt ggt gaa gca ttg gtg cgt gag att ggc gct cat gtt       1200
Leu Gln Val Ser Gly Glu Ala Leu Val Arg Glu Ile Gly Ala His Val
        225                 230                 235 gaa acc gct gac gga agg cga gtt agc gtc ggg gcg ttc ccg atc tcg       1248
Glu Thr Ala Asp Gly Arg Arg Val Ser Val Gly Ala Phe Pro Ile Ser
240                 245                 250                 255 att gat gtt gaa atg ttt ggg gag gcg tcg aaa agc gcc gtt ctt gat       1296
Ile Asp Val Glu Met Phe Gly Glu Ala Ser Lys Ser Ala Val Leu Asp
                260                 265                 270 ctt tta aaa acg ctc gac gag ccg gaa acc gta ttc ctg ggc gtt gac       1344
Leu Leu Lys Thr Leu Asp Glu Pro Glu Thr Val Phe Leu Gly Val Asp
            275                 280                 285 cga ctg gac tac acc aag ggc att ttg cag cgc ctg ctt gcg ttt gag       1392
Arg Leu Asp Tyr Thr Lys Gly Ile Leu Gln Arg Leu Leu Ala Phe Glu
        290                 295                 300 gaa ctg ctg gaa tcc ggc gcg ttg gag gcc gac aaa gct gtg ttg ctg       1440
Glu Leu Leu Glu Ser Gly Ala Leu Glu Ala Asp Lys Ala Val Leu Leu
305                 310                 315 cag gtc gcg acg cct tcg cgt gag cgc att gat cac tat cgt gtg tcg       1488
Gln Val Ala Thr Pro Ser Arg Glu Arg Ile Asp His Tyr Arg Val Ser
320                 325                 330                 335 cgt tcg cag gtc gag gaa gcc gtc ggc cgt atc aat ggt cgt ttc ggt       1536
Arg Ser Gln Val Glu Glu Ala Val Gly Arg Ile Asn Gly Arg Phe Gly
                340                 345                 350 cgc atg ggg cgt ccc gtg gtg cat tat cta cac agg tca ttg agc aaa       1584
Arg Met Gly Arg Pro Val Val His Tyr Leu His Arg Ser Leu Ser Lys
            355                 360                 365 aat gat ctc cag gtg ctg tat acc gca gcc gat gtc atg ctg gtt acg       1632
Asn Asp Leu Gln Val Leu Tyr Thr Ala Ala Asp Val Met Leu Val Thr
        370                 375                 380 cct ttt aaa gac ggt atg aac ttg gtg gct aaa gaa ttc gtg gcc aac       1680
Pro Phe Lys Asp Gly Met Asn Leu Val Ala Lys Glu Phe Val Ala Asn
        385                 390                 395 cac cgc gac ggc act ggt gct ttg gtg ctg tcc gaa ttt gcc ggc gcg       1728
His Arg Asp Gly Thr Gly Ala Leu Val Leu Ser Glu Phe Ala Gly Ala
400                 405                 410                 415 gcc act gag ctg acc ggt gcg tat tta tgc aac cca ttt gat gtg gaa       1776
Ala Thr Glu Leu Thr Gly Ala Tyr Leu Cys Asn Pro Phe Asp Val Glu
                420                 425                 430 tcc atc aaa cgg caa atg gtg gca gct gtc cat gat ttg aag cac aat       1824
Ser Ile Lys Arg Gln Met Val Ala Ala Val His Asp Leu Lys His Asn
            435                 440                 445
```

```
ccg gaa tct gcg gca acg cga atg aaa acg aac agc gag cag gtc tat    1872
Pro Glu Ser Ala Ala Thr Arg Met Lys Thr Asn Ser Glu Gln Val Tyr
        450                 455                 460 acc cac gac gtc aac gtg tgg gct aat agt ttc ctg gat tgt ttg gcg    1920
Thr His Asp Val Asn Val Trp Ala Asn Ser Phe Leu Asp Cys Leu Ala
465                 470                 475 cag tcg gga gaa aac tca tgaaccgcgc acgaatcgcg accataggcg           1968
Gln Ser Gly Glu Asn Ser
480             485 ttcttccgct tgctttactg ctggcgtcct gtggttcaga caccgtggaa atgacagatt  2028
ccacctggtt ggtgaccaat atttacaccg atccagatga gtcgaattcg atcagtaatc  2088
ttgtcatttc ccagcccagc ttagattttg gcaattcttc cctgtctggt ttcactggct  2148
gtgtgccttt tacggggcgt gcggaattct tccaaaatgg tgagcaaagc tctgttctgg  2208
atgccgatta tgtgaccttg tcttccctgg atttcgataa acttcccgat gattgccaag  2268
gacaagaact caaagttcat aacgagctgg ttgatcttct gcctggttct tttgaaatct  2328
ccaggacttc tggttcagaa atcttgctga ctagcgatgt c                     2369

<210> SEQ ID NO 30
<211> LENGTH: 485
<212> TYPE: PRT
<213> ORGANISM: Brevibacterium lactofermentum

<400> SEQUENCE: 30

Met Asp Asp Ser Asn Ser Phe Val Val Ala Asn Arg Leu Pro Val
1               5                   10                  15

Asp Met Thr Val His Pro Asp Gly Ser Tyr Ser Ile Ser Pro Ser Pro
            20                  25                  30

Gly Gly Leu Val Thr Gly Leu Ser Pro Val Leu Glu Gln His Arg Gly
        35                  40                  45

Cys Trp Val Gly Trp Pro Gly Thr Val Asp Val Ala Pro Glu Pro Phe
    50                  55                  60

Arg Thr Asp Thr Gly Val Leu His Pro Val Val Leu Thr Ala Ser
65                  70                  75                  80

Asp Tyr Glu Gly Phe Tyr Gly Phe Ser Asn Ala Thr Leu Trp Pro
                85                  90                  95

Leu Phe His Asp Leu Ile Val Thr Pro Val Tyr Asn Thr Asp Trp Trp
            100                 105                 110

His Ala Phe Arg Glu Val Asn Leu Lys Phe Ala Glu Ala Val Ser Gln
        115                 120                 125

Val Ala Ala His Gly Ala Thr Val Trp Val Gln Asp Tyr Gln Leu Leu
    130                 135                 140

Leu Val Pro Gly Ile Leu Arg Gln Met Arg Leu Asp Leu Lys Ile Gly
145                 150                 155                 160

Phe Phe Leu His Ile Pro Phe Pro Ser Pro Asp Leu Phe Arg Gln Leu
                165                 170                 175

Pro Trp Arg Glu Glu Ile Val Arg Gly Met Leu Gly Ala Asp Leu Val
            180                 185                 190

Gly Phe His Leu Val Gln Asn Ala Glu Asn Phe Leu Ala Leu Thr Gln
        195                 200                 205

Gln Val Ala Gly Thr Ala Gly Ser His Val Gly Gln Pro Asp Thr Leu
    210                 215                 220

Gln Val Ser Gly Glu Ala Leu Val Arg Glu Ile Gly Ala His Val Glu
225                 230                 235                 240
```

-continued

```
Thr Ala Asp Gly Arg Arg Val Ser Val Gly Ala Phe Pro Ile Ser Ile
            245                 250                 255

Asp Val Glu Met Phe Gly Glu Ala Ser Lys Ser Ala Val Leu Asp Leu
        260                 265                 270

Leu Lys Thr Leu Asp Glu Pro Glu Thr Val Phe Leu Gly Val Asp Arg
    275                 280                 285

Leu Asp Tyr Thr Lys Gly Ile Leu Gln Arg Leu Leu Ala Phe Glu Glu
290                 295                 300

Leu Leu Glu Ser Gly Ala Leu Glu Ala Asp Lys Ala Val Leu Leu Gln
305                 310                 315                 320

Val Ala Thr Pro Ser Arg Glu Arg Ile Asp His Tyr Arg Val Ser Arg
                325                 330                 335

Ser Gln Val Glu Glu Ala Val Gly Arg Ile Asn Gly Arg Phe Gly Arg
            340                 345                 350

Met Gly Arg Pro Val Val His Tyr Leu His Arg Ser Leu Ser Lys Asn
        355                 360                 365

Asp Leu Gln Val Leu Tyr Thr Ala Ala Asp Val Met Leu Val Thr Pro
    370                 375                 380

Phe Lys Asp Gly Met Asn Leu Val Ala Lys Glu Phe Val Ala Asn His
385                 390                 395                 400

Arg Asp Gly Thr Gly Ala Leu Val Leu Ser Glu Phe Ala Gly Ala Ala
                405                 410                 415

Thr Glu Leu Thr Gly Ala Tyr Leu Cys Asn Pro Phe Asp Val Glu Ser
            420                 425                 430

Ile Lys Arg Gln Met Val Ala Ala Val His Asp Leu Lys His Asn Pro
        435                 440                 445

Glu Ser Ala Ala Thr Arg Met Lys Thr Asn Ser Glu Gln Val Tyr Thr
    450                 455                 460

His Asp Val Asn Val Trp Ala Asn Ser Phe Leu Asp Cys Leu Ala Gln
465                 470                 475                 480

Ser Gly Glu Asn Ser
            485

<210> SEQ ID NO 31
<211> LENGTH: 2956
<212> TYPE: DNA
<213> ORGANISM: Brevibacterium lactofermentum
<220> FEATURE:
<221> NAME/KEY: CDS
<222> LOCATION: (82)..(2514)
<220> FEATURE:
<221> NAME/KEY: misc_feature
<222> LOCATION: (2953)
<223> OTHER INFORMATION: n = a or g or c or t

<400> SEQUENCE: 31
ttttcccacg cagggaaggc gtgaacacta agatcgagga cgtaccgcac gattttgcct      60
aacttttaag ggtgtttcat c atg gca cgt cca att tcc gca acg tac agg       111
                        Met Ala Arg Pro Ile Ser Ala Thr Tyr Arg
                         1               5                  10 ctt caa atg cga gga cct caa gca gat agc gcc ggg cgt ttc ttt ggt       159
Leu Gln Met Arg Gly Pro Gln Ala Asp Ser Ala Gly Arg Phe Phe Gly
             15                  20                  25 ttt gcg cag gcc aaa gcc cag ctt ccc tat ctg aag aag cta ggc atc       207
Phe Ala Gln Ala Lys Ala Gln Leu Pro Tyr Leu Lys Lys Leu Gly Ile
         30                  35                  40 agc cac ctg tac ctc tcc cct att ttt acg gcc atg cca gat tcc aat       255
Ser His Leu Tyr Leu Ser Pro Ile Phe Thr Ala Met Pro Asp Ser Asn
```

```
                  45                      50                      55
cat ggc tac gat gtc att gat ccc acc gcc atc aat gaa gag ctc ggt      303
His Gly Tyr Asp Val Ile Asp Pro Thr Ala Ile Asn Glu Glu Leu Gly
     60                  65                      70 ggc atg gag ggt ctt cga gat ctt gct gca gct aca cac gag ttg ggc      351
Gly Met Glu Gly Leu Arg Asp Leu Ala Ala Ala Thr His Glu Leu Gly
 75                  80                      85                  90 atg ggc atc atc att gat att gtt ccc aac cat tta ggt gtt gcc gtt      399
Met Gly Ile Ile Ile Asp Ile Val Pro Asn His Leu Gly Val Ala Val
                         95                     100                 105 cca cat ttg aat cct tgg tgg tgg gat gtt cta aaa aac ggc aaa gat      447
Pro His Leu Asn Pro Trp Trp Trp Asp Val Leu Lys Asn Gly Lys Asp
             110                     115                     120 tcc gct ttt gag ttc tat ttc gat att gac tgg cac gaa gac aac ggt      495
Ser Ala Phe Glu Phe Tyr Phe Asp Ile Asp Trp His Glu Asp Asn Gly
                 125                     130                     135 tct ggt ggc aag ctg ggc atg ccg att ctg ggt gct gaa ggc gat gaa      543
Ser Gly Gly Lys Leu Gly Met Pro Ile Leu Gly Ala Glu Gly Asp Glu
         140                     145                     150 gac aag ctg gaa ttc gcg gag ctt gat gga gag aaa gtg ctc aaa tat      591
Asp Lys Leu Glu Phe Ala Glu Leu Asp Gly Glu Lys Val Leu Lys Tyr
155                     160                     165                     170 ttt gac cac ctc ttc cca atc gcg cct ggt acc gaa gaa ggg aca ccg      639
Phe Asp His Leu Phe Pro Ile Ala Pro Gly Thr Glu Glu Gly Thr Pro
                     175                     180                     185 caa gaa gtc tac aag cgc cag cat tac cgc ctg cag ttc tgg cgc gac      687
Gln Glu Val Tyr Lys Arg Gln His Tyr Arg Leu Gln Phe Trp Arg Asp
                 190                     195                     200 ggc gtg atc aac ttc cgt cgc ttc ttt tcc gtg aat acg ttg gct ggc      735
Gly Val Ile Asn Phe Arg Arg Phe Phe Ser Val Asn Thr Leu Ala Gly
             205                     210                     215 atc agg caa gaa gat ccc ttg gtg ttt gaa cat act cat cgt ctg ctg      783
Ile Arg Gln Glu Asp Pro Leu Val Phe Glu His Thr His Arg Leu Leu
         220                     225                     230 cgc gaa ttg gtg gcg gaa gac ctc att gac ggc gtg cgc gtc gat cac      831
Arg Glu Leu Val Ala Glu Asp Leu Ile Asp Gly Val Arg Val Asp His
235                     240                     245                     250 ccc gac ggg ctt tcc gat cct ttt gga tat ctg cac aga ctc cgc gac      879
Pro Asp Gly Leu Ser Asp Pro Phe Gly Tyr Leu His Arg Leu Arg Asp
                     255                     260                     265 ctc att gga cct gac cgc tgg ctg atc atc gaa aag atc ttg agc gtt      927
Leu Ile Gly Pro Asp Arg Trp Leu Ile Ile Glu Lys Ile Leu Ser Val
                 270                     275                     280 gat gaa cca ctc gat ccc cgc ctg gcc gtt gat ggc acc act ggc tac      975
Asp Glu Pro Leu Asp Pro Arg Leu Ala Val Asp Gly Thr Thr Gly Tyr
             285                     290                     295 gac ccc ctc cgt gaa ctc gac ggc gtg ttt atc tcc cga gaa tct gag     1023
Asp Pro Leu Arg Glu Leu Asp Gly Val Phe Ile Ser Arg Glu Ser Glu
         300                     305                     310 gac aaa ttc tcc atg ttg gcg ctg acc cac agt gga tcc acc tgg gat     1071
Asp Lys Phe Ser Met Leu Ala Leu Thr His Ser Gly Ser Thr Trp Asp
315                     320                     325                     330 gaa cgc gcc cta aaa tcc acg gag gaa agc ctc aaa cga gtc gtc gcg     1119
Glu Arg Ala Leu Lys Ser Thr Glu Glu Ser Leu Lys Arg Val Val Ala
                     335                     340                     345 caa caa gaa ctc gca gcc gaa atc tta agg ctc gcc cgc gcc atg cgc     1167
Gln Gln Glu Leu Ala Ala Glu Ile Leu Arg Leu Ala Arg Ala Met Arg
                 350                     355                     360 cgc gat aac ttc tcc acc gca ggc acc aac gtc acc gaa gac aaa ctt     1215
```

-continued

| | | |
|---|---|---|
| Arg Asp Asn Phe Ser Thr Ala Gly Thr Asn Val Thr Glu Asp Lys Leu<br>365 370 375 | | |
| agc gaa acc atc atc gaa tta gtc gcc gcc atg ccc gtc tac cgc gcc<br>Ser Glu Thr Ile Ile Glu Leu Val Ala Ala Met Pro Val Tyr Arg Ala<br>380 385 390 | 1263 | |
| gac tac atc tcc ctc tca cgc acc acc gcc acc gtc atc gcg gag atg<br>Asp Tyr Ile Ser Leu Ser Arg Thr Thr Ala Thr Val Ile Ala Glu Met<br>395 400 405 410 | 1311 | |
| tcc aaa cgc ttc ccc tcc cgg cgc gac gca ctc gac ctc atc tcg gcc<br>Ser Lys Arg Phe Pro Ser Arg Arg Asp Ala Leu Asp Leu Ile Ser Ala<br>415 420 425 | 1359 | |
| gcc cta ctt ggc aat ggc gag gcc aaa atc cgc ttc gcc caa gtc tgc<br>Ala Leu Leu Gly Asn Gly Glu Ala Lys Ile Arg Phe Ala Gln Val Cys<br>430 435 440 | 1407 | |
| ggc gcc gtc atg gcc aaa ggt gtg gaa gac acc acc ttc tac cgc gca<br>Gly Ala Val Met Ala Lys Gly Val Glu Asp Thr Thr Phe Tyr Arg Ala<br>445 450 455 | 1455 | |
| tct agg ctc gtt gca ctg caa gaa gtc ggt ggc gcg ccg ggc agg ttc<br>Ser Arg Leu Val Ala Leu Gln Glu Val Gly Gly Ala Pro Gly Arg Phe<br>460 465 470 | 1503 | |
| ggc gtc tcc gct gca gaa ttc cac ttg ctg cag gaa gaa cgc agc ctg<br>Gly Val Ser Ala Ala Glu Phe His Leu Leu Gln Glu Glu Arg Ser Leu<br>475 480 485 490 | 1551 | |
| ctg tgg cca cgc acc atg acc acc ttg tcc acg cac gac acc aaa cgc<br>Leu Trp Pro Arg Thr Met Thr Thr Leu Ser Thr His Asp Thr Lys Arg<br>495 500 505 | 1599 | |
| ggc gaa gat acc cgc gcc cgc atc atc tcc ctg tcc gaa gtc ccc gat<br>Gly Glu Asp Thr Arg Ala Arg Ile Ile Ser Leu Ser Glu Val Pro Asp<br>510 515 520 | 1647 | |
| atg tac tcc gag ctg gtc aat cgt gtt ttc gca gtg ctc ccc gcg cca<br>Met Tyr Ser Glu Leu Val Asn Arg Val Phe Ala Val Leu Pro Ala Pro<br>525 530 535 | 1695 | |
| gac ggc gca acg ggc agt ttc ctc cta caa aac ctg ctg ggc gta tgg<br>Asp Gly Ala Thr Gly Ser Phe Leu Leu Gln Asn Leu Leu Gly Val Trp<br>540 545 550 | 1743 | |
| ccc gcc gac ggc gtg atc acc gat gcg ctg cgc gat cga ttc agg gaa<br>Pro Ala Asp Gly Val Ile Thr Asp Ala Leu Arg Asp Arg Phe Arg Glu<br>555 560 565 570 | 1791 | |
| tac gcc cta aaa gct atc cgc gaa gca tcc aca aaa acc acg tgg gtg<br>Tyr Ala Leu Lys Ala Ile Arg Glu Ala Ser Thr Lys Thr Thr Trp Val<br>575 580 585 | 1839 | |
| gac ccc aac gag tcc ttc gag gct gcg gtc tgc gat tgg gtg gaa gcg<br>Asp Pro Asn Glu Ser Phe Glu Ala Ala Val Cys Asp Trp Val Glu Ala<br>590 595 600 | 1887 | |
| ctt ttc gac gga ccc tcc acc tca tta atc acc gaa ttt gtc tcc cac<br>Leu Phe Asp Gly Pro Ser Thr Ser Leu Ile Thr Glu Phe Val Ser His<br>605 610 615 | 1935 | |
| atc aac cgt ggc tct gtg aat atc tcc tta ggt agg aaa ctg ctg caa<br>Ile Asn Arg Gly Ser Val Asn Ile Ser Leu Gly Arg Lys Leu Leu Gln<br>620 625 630 | 1983 | |
| atg gtg ggc gct gga atc ccc gac act tac caa gga act gag ttt tta<br>Met Val Gly Ala Gly Ile Pro Asp Thr Tyr Gln Gly Thr Glu Phe Leu<br>635 640 645 650 | 2031 | |
| gaa gac tcc ctg gta gat ccc gat aac cga cgc ttt gtt gat tac acc<br>Glu Asp Ser Leu Val Asp Pro Asp Asn Arg Arg Phe Val Asp Tyr Thr<br>655 660 665 | 2079 | |
| gcc aga gaa caa gtc ctg gag cgc ctg caa acc tgg gat tgg acg cag<br>Ala Arg Glu Gln Val Leu Glu Arg Leu Gln Thr Trp Asp Trp Thr Gln<br>670 675 680 | 2127 | |

-continued

```
gtt aat tcg gta gaa gac ttg gtg gat aac gcc gac atc gcc aaa atg    2175
Val Asn Ser Val Glu Asp Leu Val Asp Asn Ala Asp Ile Ala Lys Met
        685                 690                 695 gcc gtg gtc cat aaa tcc ctc gag ttg cgt gct gaa ttt cgt gca agc    2223
Ala Val Val His Lys Ser Leu Glu Leu Arg Ala Glu Phe Arg Ala Ser
700                 705                 710 ttt gtt ggt gga gat cat cag gca gta ttt ggc gaa ggt cgc gca gaa    2271
Phe Val Gly Gly Asp His Gln Ala Val Phe Gly Glu Gly Arg Ala Glu
715                 720                 725                 730 tcc cac atc atg ggc atc gcc cgc ggt aca gac cga aac cac ctc aac    2319
Ser His Ile Met Gly Ile Ala Arg Gly Thr Asp Arg Asn His Leu Asn
            735                 740                 745 atc att gct ctt gct acc cgt cga cca ctg atc ttg gaa gac cgt ggc    2367
Ile Ile Ala Leu Ala Thr Arg Arg Pro Leu Ile Leu Glu Asp Arg Gly
        750                 755                 760 gga tgg tat gac acc acc gtc acg ctt cct ggt gga caa tgg gaa gac    2415
Gly Trp Tyr Asp Thr Thr Val Thr Leu Pro Gly Gly Gln Trp Glu Asp
765                 770                 775 agg ctc acc ggg caa cgc ttc agt ggt gtt gtc cca gcc acc gat ttg    2463
Arg Leu Thr Gly Gln Arg Phe Ser Gly Val Val Pro Ala Thr Asp Leu
780                 785                 790 ttc tca cat tta ccc gta tct ttg ttg gtt tta gta ccc gat agt gag    2511
Phe Ser His Leu Pro Val Ser Leu Leu Val Leu Val Pro Asp Ser Glu
795                 800                 805                 810 ttt tgatccctgc acaggaaagt tagcggcgct actatgaacg atcgatatgt         2564
Phe ctgacaacac tctctcccaa tttggcagtt actaccacga attccgacgt gcccatccca  2624
tggccgacgt cgaattcctc ctagcaattg aagaattact cacagacggt ggtgtcacct  2684
tcgatcgcgt caccacacgc atcaaagaat ggtcaagcct gaaagccaag gctcgcaagc  2744
gtcgcgacga tggctcgttg atctaccctg atccgcgcaa agacatccac gacatgatcg  2804
gtgttcggat caccacgtac cactccacgg aaattcccgt ggccttaaaa gtgctccaag  2864
actccttcat cgtccacaaa tccgtagaca agccgctga aactcgcatc tcaggcggct    2924
ttggttacgg ctcccaccac caaggattnt ag                                2956
```

<210> SEQ ID NO 32
<211> LENGTH: 811
<212> TYPE: PRT
<213> ORGANISM: Brevibacterium lactofermentum

<400> SEQUENCE: 32

```
Met Ala Arg Pro Ile Ser Ala Thr Tyr Arg Leu Gln Met Arg Gly Pro
1               5                   10                  15

Gln Ala Asp Ser Ala Gly Arg Phe Phe Gly Phe Ala Gln Ala Lys Ala
            20                  25                  30

Gln Leu Pro Tyr Leu Lys Lys Leu Gly Ile Ser His Leu Tyr Leu Ser
        35                  40                  45

Pro Ile Phe Thr Ala Met Pro Asp Ser Asn His Gly Tyr Asp Val Ile
    50                  55                  60

Asp Pro Thr Ala Ile Asn Glu Glu Leu Gly Met Glu Gly Leu Arg
65                  70                  75                  80

Asp Leu Ala Ala Ala Thr His Glu Leu Gly Met Gly Ile Ile Ile Asp
            85                  90                  95

Ile Val Pro Asn His Leu Gly Val Ala Val Pro His Leu Asn Pro Trp
            100                 105                 110

Trp Trp Asp Val Leu Lys Asn Gly Lys Asp Ser Ala Phe Glu Phe Tyr
```

```
              115                 120                 125
Phe Asp Ile Asp Trp His Glu Asp Asn Gly Ser Gly Gly Lys Leu Gly
    130                 135                 140
Met Pro Ile Leu Gly Ala Glu Gly Asp Glu Asp Lys Leu Glu Phe Ala
145                 150                 155                 160
Glu Leu Asp Gly Glu Lys Val Leu Lys Tyr Phe Asp His Leu Phe Pro
                165                 170                 175
Ile Ala Pro Gly Thr Glu Gly Thr Pro Gln Glu Val Tyr Lys Arg
                180                 185                 190
Gln His Tyr Arg Leu Gln Phe Trp Arg Asp Gly Val Ile Asn Phe Arg
            195                 200                 205
Arg Phe Phe Ser Val Asn Thr Leu Ala Gly Ile Arg Gln Glu Asp Pro
    210                 215                 220
Leu Val Phe Glu His Thr His Arg Leu Leu Arg Glu Leu Val Ala Glu
225                 230                 235                 240
Asp Leu Ile Asp Gly Val Arg Val Asp His Pro Asp Gly Leu Ser Asp
                245                 250                 255
Pro Phe Gly Tyr Leu His Arg Leu Arg Asp Leu Ile Gly Pro Asp Arg
                260                 265                 270
Trp Leu Ile Ile Glu Lys Ile Leu Ser Val Asp Glu Pro Leu Asp Pro
            275                 280                 285
Arg Leu Ala Val Asp Gly Thr Thr Gly Tyr Asp Pro Leu Arg Glu Leu
    290                 295                 300
Asp Gly Val Phe Ile Ser Arg Glu Ser Glu Asp Lys Phe Ser Met Leu
305                 310                 315                 320
Ala Leu Thr His Ser Gly Ser Thr Trp Asp Glu Arg Ala Leu Lys Ser
                325                 330                 335
Thr Glu Glu Ser Leu Lys Arg Val Val Ala Gln Gln Glu Leu Ala Ala
                340                 345                 350
Glu Ile Leu Arg Leu Ala Arg Ala Met Arg Arg Asp Asn Phe Ser Thr
            355                 360                 365
Ala Gly Thr Asn Val Thr Glu Asp Lys Leu Ser Glu Thr Ile Ile Glu
    370                 375                 380
Leu Val Ala Ala Met Pro Val Tyr Arg Ala Asp Tyr Ile Ser Leu Ser
385                 390                 395                 400
Arg Thr Thr Ala Thr Val Ile Ala Glu Met Ser Lys Arg Phe Pro Ser
                405                 410                 415
Arg Arg Asp Ala Leu Asp Leu Ile Ser Ala Ala Leu Leu Gly Asn Gly
                420                 425                 430
Glu Ala Lys Ile Arg Phe Ala Gln Val Cys Gly Ala Val Met Ala Lys
            435                 440                 445
Gly Val Glu Asp Thr Thr Phe Tyr Arg Ala Ser Arg Leu Val Ala Leu
    450                 455                 460
Gln Glu Val Gly Gly Ala Pro Gly Arg Phe Gly Val Ser Ala Ala Glu
465                 470                 475                 480
Phe His Leu Leu Gln Glu Glu Arg Ser Leu Leu Trp Pro Arg Thr Met
                485                 490                 495
Thr Thr Leu Ser Thr His Asp Thr Lys Arg Gly Glu Asp Thr Arg Ala
                500                 505                 510
Arg Ile Ile Ser Leu Ser Glu Val Pro Asp Met Tyr Ser Glu Leu Val
            515                 520                 525
Asn Arg Val Phe Ala Val Leu Pro Ala Pro Asp Gly Ala Thr Gly Ser
    530                 535                 540
```

```
Phe Leu Leu Gln Asn Leu Leu Gly Val Trp Pro Ala Asp Gly Val Ile
545                 550                 555                 560

Thr Asp Ala Leu Arg Asp Arg Phe Arg Glu Tyr Ala Leu Lys Ala Ile
            565                 570                 575

Arg Glu Ala Ser Thr Lys Thr Thr Trp Val Asp Pro Asn Glu Ser Phe
        580                 585                 590

Glu Ala Ala Val Cys Asp Trp Val Glu Ala Leu Phe Asp Gly Pro Ser
    595                 600                 605

Thr Ser Leu Ile Thr Glu Phe Val Ser His Ile Asn Arg Gly Ser Val
610                 615                 620

Asn Ile Ser Leu Gly Arg Lys Leu Leu Gln Met Val Gly Ala Gly Ile
625                 630                 635                 640

Pro Asp Thr Tyr Gln Gly Thr Glu Phe Leu Glu Asp Ser Leu Val Asp
            645                 650                 655

Pro Asp Asn Arg Arg Phe Val Asp Tyr Thr Ala Arg Glu Gln Val Leu
        660                 665                 670

Glu Arg Leu Gln Thr Trp Asp Trp Thr Gln Val Asn Ser Val Glu Asp
    675                 680                 685

Leu Val Asp Asn Ala Asp Ile Ala Lys Met Ala Val Val His Lys Ser
690                 695                 700

Leu Glu Leu Arg Ala Glu Phe Arg Ala Ser Phe Val Gly Gly Asp His
705                 710                 715                 720

Gln Ala Val Phe Gly Glu Gly Arg Ala Glu Ser His Ile Met Gly Ile
            725                 730                 735

Ala Arg Gly Thr Asp Arg Asn His Leu Asn Ile Ile Ala Leu Ala Thr
        740                 745                 750

Arg Arg Pro Leu Ile Leu Glu Asp Arg Gly Gly Trp Tyr Asp Thr Thr
    755                 760                 765

Val Thr Leu Pro Gly Gly Gln Trp Glu Asp Arg Leu Thr Gly Gln Arg
770                 775                 780

Phe Ser Gly Val Val Pro Ala Thr Asp Leu Phe Ser His Leu Pro Val
785                 790                 795                 800

Ser Leu Leu Val Leu Val Pro Asp Ser Glu Phe
            805                 810
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: primer for PCR

<400> SEQUENCE: 33
ccaaaatcga taacatcaat cgagatcggg                30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: primer for PCR

<400> SEQUENCE: 34
cttgatcgat taaaaacgct cgacgagccg                30

US 7,307,160 B1

OTSA GENE ENCODING TREHALOSE-6-PHOSPHATE SYNTHASE FROM A CORYNEFORM BACTERIUM

This application is a divisional application of U.S. patent application Ser. No. 09/895,382, filed Jul. 2, 2001, now abandoned the entire contents of which are hereby incorporated by reference in its entirety.

BACKGROUND OF THE INVENTION

1. Field of the Invention

The present invention relates to a novel L-glutamic acid producing bacterium and a method for producing L-glutamic acid by fermentation utilizing it. L-glutamic acid is an important amino acid as foodstuffs, drugs and so forth.

2. Description of the Related Art

Conventionally, L-glutamic acid is mainly produced by fermentative methods using so-called L-glutamic acid producing coryneform bacteria belonging to the genus *Brevibacterium*, *Corynebacterium* or *Microbacterium*, or mutant strains thereof (Amino Acid Fermentation, pp. 195–215, Gakkai Shuppan Center, 1986).

It is known that, in the production of L-glutamic acid by fermentation, trehalose is also produced as a secondary product. Therefore, techniques have been developed for decomposing or metabolizing the produced trehalose. Such techniques include the method of producing an amino acid by fermentation using a coryneform bacterium in which proliferation ability on trehalose is induced (Japanese Patent Laid-open (Kokai) No. 5-276935) and the method of producing amino acid by fermentation using a coryneform bacterium in which a gene coding for trehalose catabolic enzyme is amplified (Korean Patent Publication (B1) No. 165836). However, it is not known how to suppress the formation of trehalose itself in an L-glutamic acid producing bacterium.

In *Escherichia coli*, the synthesis of trehalose is catalyzed by trehalose-6-phosphate synthase. This enzyme is known to be encoded by otsA gene. Further, it has been also reported that an otsA gene-disrupted strain of *Escherichia coli* can scarcely grow in a hyperosmotic medium (H. M. Glaever, et al., *J. Bacteriol.*, 170(6), 2841–2849. (1998)). However, the relationship between disruption of otsA gene and production of substances has not been known.

On the other hand, although the treY gene is known for *Brevibacterium helvolum* among bacteria belonging to the genus *Brevibacterium* bacteria, any otsA gene is not known for them. As for bacteria belonging to the genus *Mycobacterium* bacteria, there is known a pathway via a reaction catalyzed by a product encoded by treS gene (trehalose synthase (TreS)), which gene is different from the otsA gene and treY gene, as a gene coding for a enzyme in trehalose biosynthesis pathway (De Smet K. A., et al., Microbiology, 146 (1), 199–208 (2000)). However, this pathway utilizes maltose as a substrate and does not relate to usual L-glutamic acid fermentation that utilizes glucose, fructose or sucrose as a starting material.

SUMMARY OF THE INVENTION

An object of the present invention is to improve production efficiency of L-glutamic acid in L-glutamic acid production by fermentation using coryneform bacteria through suppression of the production of trehalose as a secondary product.

The inventors of the present invention assiduously studied in order to achieve the aforementioned object. As a result, they found that bacterium belonging to the genus *Brevibacterium* contained otsA gene and treY gene like *Mycobacterium tuberculosis*, and the production efficiency of L-glutamic acid was improved by disrupting at least one of these genes. Thus, they accomplished the present invention.

That is, the present invention provides the followings.

(1) A coryneform bacterium having L-glutamic acid producing ability, wherein trehalose synthesis ability is decreased or deleted in the bacterium.

(2) The coryneform bacteria according to (1), wherein the trehalose synthesis ability is decreased or deleted by introducing a mutation into a chromosomal gene coding for an enzyme in a trehalose synthesis pathway or disrupting the gene.

(3) The coryneform bacteria according to (2), wherein the gene coding for the enzyme in trehalose synthesis pathway consists of a gene coding for trehalose-6-phosphate synthase, a gene coding for maltooligosyltrehalose synthase, or both of these genes.

(4) The coryneform bacteria according to (3), wherein the gene coding for trehalose-6-phosphate synthase codes for the amino acid sequence of SEQ ID NO: 30, and the gene coding for maltooligosyltrehalose synthase codes for the amino acid sequence of SEQ ID NO: 32.

(5) A method for producing L-glutamic acid comprising culturing a coryneform bacterium according to any one of (1) to (4) in a medium to produce and accumulate L-glutamic acid in the medium, and collecting the L-glutamic acid from the medium.

(6) A DNA coding for a protein defined in the following (A) or (B):

(A) a protein having the amino acid sequence of SEQ ID NO: 30, (B) a protein having an amino acid sequence of SEQ ID NO: 30 including substitution, deletion, insertion or addition of one or several amino acid residues and having trehalose-6-phosphate synthase activity.

(7) A DNA according to (6), which is a DNA defined in the following (a) or (b):

(a) a DNA containing a nucleotide sequence comprising at least the residues of nucleotide numbers 484–1938 in the nucleotide sequence of SEQ ID NO: 29, (b) a DNA hybridizable with a nucleotide sequence comprising at least the residues of nucleotide numbers 484–1938 in the nucleotide sequence of SEQ ID NO: 29 under a stringent condition, showing homology of 55% or more to the foregoing nucleotide sequence, and coding for a protein having trehalose-6-phosphate synthase activity.

(8) A DNA coding for a protein defined in the following (A) or (B):

(A) a protein having the amino acid sequence of SEQ ID NO: 32, (B) a protein having an amino acid sequence, of SEQ ID NO: 32 including substitution, deletion, insertion or addition of one or several amino acid residues and having maltooligosyltrehalose synthase activity.

(9) A DNA according to (8), which is a DNA defined in the following (a) or (b):

(a) a DNA containing a nucleotide sequence comprising at least the residues of nucleotide numbers 82–2514 in the nucleotide sequence of SEQ ID NO: 31, (b) a DNA hybridizable with a nucleotide sequence comprising at least the residues of nucleotide numbers 82–2514 in the nucleotide sequence of SEQ ID NO: 31 under a stringent condition, showing homology of 60% or more to the foregoing nucleotide sequence, and coding for a protein having maltooligosyltrehalose synthase activity.

The trehalose-6-phosphate synthase activity means an activity to catalyze a reaction in which α,α-trehalose-6-phosphate and UDP are produced from UDP-glucose and glucose-6-phosphate, and the maltooligosyltrehalose synthase activity means an activity to catalyze a reaction in which maltotriosyltrehalose is produced from maltopentose.

According to the present invention, production efficiency of L-glutamic acid in L-glutamic acid production by fermentation using coryneform bacteria can be improved through inhibition of the production of trehalose as a secondary product.

PREFERRED EMBODIMENTS OF THE INVENTION

Hereafter, the present invention will be explained in detail.

The coryneform bacterium of the present invention is a coryneform bacterium having L-glutamic acid producing ability, in which trehalose synthesis ability is decreased or deleted.

The coryneform bacteria referred to in the present invention include the group of microorganisms defined in Bergey's Manual of Determinative Bacteriology, 8th edition, p. 599 (1974), which are aerobic Gram-positive rods having no acid resistance and no spore-forming ability aerobic. They have hitherto been classified into the genus *Brevibacterium*, but united into the genus *Corynebacterium* at present (*Int. J. Syst. Bacteriol.*, 41, 255 (1981)), and include bacteria belonging to the genus *Brevibacterium* or *Microbacterium* closely relative to the genus *Corynebacterium*. Examples of such coryneform bacteria are mentioned below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes* (*Corynebacterium ammoniagenes*)
*Brevibacterium album*
*Brevibacterium cerium*
*Microbacterium ammoniaphilum*

Specifically, the following strains can be exemplified.
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, 13032, 13060
*Corynebacterium lilium* (*Corynebacterium glutamicum*) ATCC 15990
*Corynebacterium melassecola* ATCC 17965
*Corynebacterium thermoaminogenes* AJ12340 (FERM BP-1539)
*Corynebacterium herculis* ATCC13868
*Brevibacterium divaricatum* (*Corynebacterium glutamicum*) ATCC 14020
*Brevibacterium flavum* (*Corynebacterium glutamicum*) ATCC 13826, ATCC 14067
*Brevibacterium immariophilum* ATCC 14068
*Brevibacterium lactofermentum* (*Corynebacterium glutamicum*) ATCC 13665, ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* (*Corynebacterium ammoniagenes*) ATCC 6871
*Brevibacterium album* ATCC 15111
*Brevibacterium cerium* ATCC 15112
*Microbacterium ammoniaphilum* ATCC 15354

The trehalose synthesis ability of such coryneform bacteria as mentioned above can be decreased or deleted by mutagenizing or disrupting a gene coding for an enzyme in trehalose synthesis pathway using mutagenesis treatment or genetic recombination technique. Such a mutation may be a mutation that suppresses transcription or translation of the gene coding for the enzyme in trehalose synthesis pathway, or a mutation that causes elimination or decrease of an enzyme in trehalose systhesis pathway. The enzyme in trehalose systhesis pathway may be exemplified by, for example, trehalose-6-phosphate synthase, maltooligosyltrehalose synthases, or both of these.

The disruption of a gene coding for an enzyme in trehalose systhesis pathway can be performed by gene substitution utilizing homologous recombination. A gene on a chromosome of a coryneform bacterium can be disrupted by transforming the coryneform bacterium with DNA containing a gene coding for an enzyme in trehalose systhesis pathway modified so that a part thereof should be deleted and hence the enzyme in trehalose systhesis pathway should not normally function (deletion type gene), and allowing recombination between the deletion type gene and a normal gene on the chromosome. Such gene disruption by homologous recombination has already been established. To this end, there can be mentioned a method utilizing a linear DNA or a cyclic DNA that does not replicate in coryneform bacteria and a method utilizing a plasmid containing a temperature sensitive replication origin. However, a method utilizing a cyclic DNA that does not replicate in coryneform bacteria or a plasmid containing a temperature sensitive replication origin is preferred.

The gene coding for an enzyme in trehalose systhesis pathway may be exemplified by, for example, the otsA gene or treY gene, or it may consist of both of these. Since the nucleotide sequences of the otsA gene and treY gene of *Brevibacterium lactofermentum* and flanking regions thereof have been elucidated by the present invention, those genes can be easily obtained by preparing primers based on the sequences and performing PCR (polymerase chain reaction, see White, T. J. et al., *Trends Genet.*, 5, 185 (1989)) using the primers and chromosomal DNA of *Brevibacterium lactofermentum* as a template.

The nucleotide sequence comprising the otsA gene and the nucleotide sequence comprising the treY gene of *Brevibacterium lactofermentum* obtained in the examples described later are shown in SEQ ID NOS: 29 and 31, respectively. Further, the amino acid sequences encoded by these nucleotide sequences are shown in SEQ ID NOS: 30 and 32, respectively.

The otsA gene and treY gene each may be one coding for a protein including substitution, deletion, insertion or addition of one or several amino acids at one or a plurality of positions, provided that the activity of trehalose-6-phosphate synthase or maltooligosyltrehalose synthase encoded thereby is not deteriorated. While the number of "several" amino acids differs depending on positions or types of amino acid residues in the three-dimensional structure of the protein, it is preferably 1–40, more preferably 1–20, further preferably 1–10.

A DNA coding for the substantially same protein as trehalose-6-phosphate synthase or maltooligosyltrehalose synthase described above can be obtained by, for example, modifying each of the nucleotide sequences by, for example, the site-directed mutagenesis method so that one or more amino acid residues at a specified site should involve substitution, deletion, insertion, addition or inversion. Such a DNA modified as described above may also be obtained by a conventionally known mutation treatment. The mutation treatment includes a method of treating DNA coding for trehalose-6-phosphate synthase or maltooligosyltrehalose in vitro, for example, with hydroxylamine, and a method for treating a microorganism, for example, a bacterium belonging to the genus *Escherichia* harboring a DNA coding for trehalose-6-phosphate synthase or maltooligosyltrehalose with ultraviolet irradiation or a mutating agent usually used for mutation treatment such as N-methyl-N'-nitro-N-nitrosoguanidine (NTG) and nitrous acid.

The substitution, deletion, insertion, addition, or inversion of nucleotide as described above also includes a naturally occurring mutant or variant on the basis of, for example, individual difference or difference in species or genus of microorganisms that harbor trehalose-6-phosphate synthase or maltooligosyltrehalose.

A DNA coding for the substantially same protein as trehalose-6-phosphate synthase or maltooligosyltrehalose synthase described above can be obtained by expressing such a DNA having a mutation as described above in a suitable cell, and examining the trehalose-6-phosphate synthase activity or maltooligosyltrehalose synthase activity of the expression product.

A DNA coding for substantially the same protein as trehalose-6-phosphate synthase can also be obtained by isolating a DNA hybridizable with a DNA having, for example, a nucleotide sequence corresponding to nucleotide numbers of 484–1938 of the nucleotide sequence shown in SEQ ID NO: 29 or a probe that can be prepared from the nucleotide sequence under a stringent condition, showing homology of 55% or more, preferably 65% or more, more preferably 75% or more, to the foregoing nucleotide sequence, and having trehalose-6-phosphate synthase activity from a DNA coding for trehalose-6-phosphate synthase having a mutation or from a cell harboring it. Similarly, a DNA coding for substantially the same protein as maltooligosyltrehalose synthase can also be obtained by isolating a DNA hybridizable with a DNA having, for example, a nucleotide sequence corresponding to nucleotide numbers of 82–2514 of the nucleotide sequence shown in SEQ ID NO: 31 or a probe that can be prepared from the nucleotide sequence under a stringent condition, showing homology of 60% or more, preferably 70% or more, more preferably 80% or more, to the foregoing nucleotide sequence, and having maltooligosyltrehalose synthase activity from a DNA coding for maltooligosyltrehalose synthase having a mutation or from a cell harboring it.

The "stringent condition" referred to herein is a condition under which so-called specific hybrid is formed, and non-specific hybrid is not formed. It is difficult to clearly express this condition by using any numerical value. However, for example, the stringent condition includes a condition under which DNA's having high homology, for example, DNA's having homology of not less than 55%, preferably not less than 60%, are hybridized with each other, and DNA's having homology lower than the above level are not hybridized with each other. Alternatively, the stringent condition is exemplified by a condition under which DNA's are hybridized with each other at a salt concentration corresponding to an ordinary condition of washing in Southern hybridization, i.e., 1×SSC, 0.1% SDS, preferably 0.1×SSC, 0.1% SDS, at 60° C.

As the probe, a partial sequence of each gene can also be used. Such a probe can be produced by PCR using oligonucleotides produced based on the nucleotide sequence of each gene as primers and a DNA fragment containing each gene as a template. When a DNA fragment in a length of about 300 bp is used as the probe, the washing conditions for the hybridization may consists of 50° C., 2×SSC and 0.1% SDS.

Genes hybridizable under such conditions as described above include those having a stop codon generated in a coding region of the genes, and those having no activity due to mutation of active center. However, such mutants can be easily removed by ligating each of the genes with a commercially available expression vector, and measuring trehalose-6-phosphate synthase activity or maltooligosyltrehalose synthase activity.

When an otsA gene or treY gene is used for the disruption of these genes on chromosomes of coryneform bacteria, the encoded trehalose-6-phosphate synthase or maltooligosyltrehalose synthase are not required to have their activities. Further, the otsA gene or treY gene used for the gene disruption may be a gene derived from another microorganism, so long as they can undergo homologous recombination with these genes of coryneform bacteria. For example, an otsA gene of bacterium belonging to the genus *Escherichia* or *Mycobacterium*, treY gene of bacterium belonging to the genus *Arthrobacter, Brevibacterium helvolum*, or bacterium belonging to the genus *Rhizobium* can be mentioned.

A deletion type gene of the otsA gene or treY gene can be prepared by excising a certain region with restriction enzyme(s) from a DNA fragment containing one of these genes or a part of them to delete at least a part of coding region or an expression regulatory sequence such as promoter.

Further, a deletion type gene can also be obtained by performing PCR using primers designed so that a part of gene should be deleted. Furthermore, a deletion type gene may be one obtained by single nucleotide mutation, for example, a frame shift mutation.

Gene disruption of the otsA gene will be explained hereafter. Gene disruption of the treY gene can be performed similarly.

An otsA gene on a host chromosome can be replaced with a deletion type otsA gene as follows. That is, a deletion type otsA gene and a marker gene for resistance to a drug, such as kanamycin, chloramphenicol, tetracycline and streptomycin, are inserted into a plasmid that cannot autonomously replicate in coryneform bacteria to prepare a recombinant DNA. A coryneform bacterium can be transformed with the recombinant DNA, and the transformant strain can be cultured in a medium containing the drug to obtain a transformant strain in which the recombinant DNA was introduced into chromosomal DNA. Alternatively, such a transformant strain can be obtained by using a temperature sensitive plasmid as the plasmid, and culturing the transformants at a temperature at which the temperature sensitive plasmid cannot replicate.

In a strain in which the recombinant DNA is incorporated into a chromosome as described above, the recombinant DNA causes recombination with an otsA gene sequence that originally exists on the chromosome, and two of fused genes comprising the chromosomal otsA gene and the deletion type otsA gene are inserted into the chromosome so that other portions of the recombinant DNA (vector portion and drug resistance marker gene) should be interposed between them.

Then, in order to leave only the deletion type otsA gene on the chromosomal DNA, one copy of the otsA gene is eliminated from the chromosomal DNA together with the vector portion (including the drug resistance marker gene) by recombination of two of the otsA genes. In that case, the normal otsA gene is left on the chromosomal DNA and the deletion type otsA gene is excised, or conversely, the deletion type otsA gene is left on the chromosomal DNA and the normal otsA gene is excised. It can be confirmed which type of the gene is left on the chromosomal DNA by investigating structure of the otsA gene on the chromosome by PCR, hybridization or the like.

The coryneform bacterium used for the present invention may have enhanced activity of an enzyme that catalyzes the biosynthesis of L-glutamic acid in addition to the deletion or decrease of trehalose synthesis ability. Examples of the enzyme that catalyzes the biosynthesis of L-glutamic acid include glutamate dehydrogenase, glutamine synthetase, glutamate synthase, isocitrate dehydrogenase, aconitate hydratase, citrate synthase, pyruvate carboxylase, phosphoenolpyruvate carboxylase, phosphoenolpyruvate synthase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and so forth.

Further, in the coryneform bacterium used for the present invention, an enzyme that catalyzes a reaction for generating a compound other than L-glutamic acid by branching off from the biosynthetic pathway of L-glutamic acid may be declined or made deficient. Examples of such an enzyme include a-ketoglutarate dehydrogenase, isocitrate lyase, phosphate acetyltransferase, acetate kinase, acetohydroxiamate synthase, acetolactate synthase, formate acetyltransferase, lactate dehydrogenase, L-glutamate decarboxylase, 1-pyrroline dehydrogenase and so forth.

Furthermore, by introducing a temperature sensitive mutation for a biotin activity inhibiting substance such as surface active agents into a coryneform bacterium having L-glutamic acid producing ability, the bacterium becomes to be able to produce L-glutamic acid in a medium containing an excessive amount of biotin in the absence of a biotin activity inhibiting substance (see WO96/06180). As such a coryneform bacterium, the Brevibacterium lactofermentum AJ13029 strain disclosed in WO96/06180 can be mentioned. The AJ13029 strain was deposited at the National Institute of Bioscience and Human-Technology, Agency of Industrial Science and Technology (currently, the independent administrative corporation, National Institute of Advanced Industrial Science and Technology, International Patent Organism Depositary (Chuo Dai-6, 1-1 Higashi 1-Chome, Tsukuba-shi, Ibaraki-ken, Japan, postal code: 305-5466) on Sep. 2, 1994, and received an accession number of FERM P-14501. Then, it was transferred to an international deposit under the provisions of the Budapest Treaty on Aug. 1, 1995, and received an accession number of FERM BP-5189.

When a coryneform bacterium having L-glutamic acid producing ability, in which trehalose synthesis ability is decreased or deleted, is cultured in a suitable medium, L-glutamic acid is accumulated in the medium.

The medium used for producing L-glutamic acid is a usual medium that contains a carbon source, a nitrogen source, inorganic ions and other organic trace nutrients as required. As the carbon source, it is possible to use sugars such as glucose, lactose, galactose, fructose, sucrose, maltose, blackstrap molasses and starch hydrolysate; alcohols such as ethanol and inositol; or organic acids such as acetic acid, fumaric acid, citric acid and succinic acid.

As the nitrogen source, there can be used inorganic ammonium salts such as ammonium sulfate, ammonium nitrate, ammonium chloride, ammonium phosphate and ammonium acetate, ammonia, organic nitrogen such as peptone, meat extract, yeast extract, corn steep liquor and soybean hydrolysate, ammonia gas, aqueous ammonia and so forth.

As the inorganic ions (or sources thereof), added is a small amount of potassium phosphate, magnesium sulfate, iron ions, manganese ions and so forth. As for the organic trace nutrients, it is desirable to add required substances such as vitamin $B_1$, yeast extract and so forth in a suitable amount as required.

The culture is preferably performed under an aerobic condition performed by shaking, stirring for aeration or the like for 16 to 72 hours. The culture temperature is controlled to be at 30° C. to 45° C., and pH is controlled to be 5 to 9 during the culture. For such adjustment of pH, inorganic or organic acidic or alkaline substances, ammonia gas and so forth can be used.

Collection of L-glutamic acid from fermentation broth can be performed by, for example, methods utilizing ion exchange resins, crystallization and so forth. Specifically, L-glutamic acid can be adsorbed on an anion exchange resin and isolated from it, or crystallized by neutralization.

EXAMPLES

Hereafter, the present invention will be explained more specifically with reference to the following examples.

Example 1

Construction of otsA Gene-Disrupted Strain of *Brevibacterium lactofermentum*

<1> Cloning of otsA Gene

Since otsA gene of *Brevibacterium lactofermentum* was not known, it was obtained by utilizing a nucleotide sequence of otsA gene of another microorganism for reference. The otsA genes of *Escherichia* and *Mycobacterium* had been hitherto elucidated for their entire nucleotide sequences (Kaasen I., et al., Gene, 145 (1), 9–15 (1994); De Smet K. A., et al., Microbiology, 146 (1), 199–208 (2000)). Therefore, referring to an amino acid sequence deduced from these nucleotide sequences, DNA primers P1 (SEQ ID NO: 1) and P2 (SEQ ID NO: 2) for PCR were synthesized first. The DNA primers P1 and P2 corresponded to the regions of the nucleotide numbers of 1894–1913 and 2531–2549 of the nucleotide sequence of the otsA gene of *Escherichia coli* (GenBank accession X69160), respectively. They also corresponded to the regions of the nucleotide numbers 40499–40518 and 41166–41184 of the otsA gene of *Mycobacterium tuberculosis* (GenBank accession Z95390), respectively.

Then, PCR was performed by using the primers P1 and P2 and chromosomal DNA of *Brevibacterium lactofermentum* ATCC 13869 as a template with a cycle consisting of reactions at 94° C. for 0.5 minute, 50° C. for 0.5 minute and 72° C. for 4 minutes, which was repeated for 30 cycles. As a result, a substantially single kind of amplified fragment of about 0.6 kbp was obtained. This amplified fragment was cloned into a plasmid vector pCR2.1 by using "Original TA Cloning Kit" produced by Invitrogen to obtain pCotsA. Then, the nucleotide sequence of the cloned fragment was determined.

Based on the nucleotide sequence of the partial fragment of otsA gene obtained as described above, DNA primers P10 (SEQ ID NO: 8) and P12 (SEQ ID NO: 10) were newly synthesized, and unknown regions flanking to the partial fragment was amplified by "inverse PCR" (Triglia, T. et al., *Nucleic Acids Res.*, 16, 81–86 (1988); Ochman H., et al., *Genetics*, 120, 621–623 (1988)). The chromosomal DNA of *Brevibacterium lactofermentum* ATCC 13869 was digested with a restriction enzyme BamHI, BglII, ClaI, HindIII, KpnI, MluI, MunL, SalI or XhoI, and self-ligated by using T4 DNA ligase (Takara Shuzo). By using resultant DNA as a template and the DNA primers P10 and P12, PCR was performed with a cycle consisting of reactions at 94° C. for 0.5 minute, 55° C. for 1 minute and 72° C. for 4 minutes, which was repeated for 30 cycles. As a result, when ClaI or BglII was used as the restriction enzyme, an amplified fragment of 4 kbp was obtained for each case. The nucleotide sequences of these amplified fragments were directly determined by using the DNA primers P5 to P9 (SEQ ID NOS: 3–7) and P11 to P15 (SEQ ID NOS: 9–13). Thus, the entire nucleotide sequence of otsA gene of *Brevibacterium lactofermentum* ATCC 13869 was determined as shown in SEQ ID NO: 29. The amino acid sequence encoded by this nucleotide sequence is shown in SEQ ID NOS: 29 and 30.

When homology of the sequence of the aforementioned otsA gene was determined with respect to the otsA gene of *Escherichia coli* (GenBank accession X69160) and the otsA gene of *Mycobacterium tuberculosis* (GenBank accession Z95390), the nucleotide sequence showed homologies of 46.3% and 55.9%, respectively, and the amino acid sequence showed homologies of 30.9% and 51.7%, respectively. The homologies were calculated by using software, "GENETIX-WIN" (Software Development), based on the Lipman-Person method (*Science*, 227, 1435–1441 (1985)).

<2> Preparation of Plasmid for otsA Gene Disruption

In order to examine presence or absence of improvement effect in L-glutamic acid productivity by disruption of a gene coding for an enzyme in trehalose biosythesis pathway in coryneform bacteria, a plasmid for otsA gene disruption was produced. A plasmid for otsA gene disruption was produced as follows. PCR was performed by using the plasmid pCotsA previously constructed in the cloning of the otsA gene as a template and the primers P29 (SEQ ID NO: 33) and P30 (SEQ ID NO: 34) comprising ClaI site with a cycle consisting of reactions at 94° C. for 0.5 minute, 55° C. for 0.5 minute and 72° C. for 8 minutes, which was repeated for 30 cycles. The amplified fragment was digested with ClaI, blunt-ended by using T4 DNA polymerase (Takara Shuzo), and self-ligated by using T4 ligase (Takara Shuzo) to construct a plasmid pCotsAC containing the otsA gene having a frame shift mutation (1258–1300th nucleotides of SEQ ID NO: 29 were deleted) at an approximately central part thereof.

<3> Preparation of otsA Gene-Disrupted Strain

By using the plasmid pCotsAC for gene disruption, a L-glutamic acid producing bacterium, *Brevibacterium lactofermentum* ATCC 13869, was transformed by the electric pulse method, and transformants were selected as to the ability to grow in CM2B medium containing 20 mg/L of kanamycin. Because the plasmid pCotsAC for otsA gene disruption did not have a replication origin that could function in *Brevibacterium lactofermentum*, resultant transformants obtained by using the plasmid suffered homologous recombination occurred between the otsA genes on the chromosome of *Brevibacterium lactofermentum* and the plasmid pCotsAC for gene disruption. From the homologous recombinant strains obtained as described above, strains in which the vector portion of the plasmid pCotsAC for gene disruption was eliminated due to re-occurrence of homologous recombination were selected based on acquired kanamycin sensitivity as a marker.

From the strains obtained as described above, a strain introduced with the desired frame shift mutation was selected. Selection of such a strain was performed by PCR using chromosomal DNA extracted from a strain that became kanamycin sensitive as a template and the DNA primers P8 (SEQ ID NO: 14) and P13 (SEQ ID NO: 11) with a cycle consisting of reactions at 94° C. for 0.5 minute, 55° C. for 0.5 minute and 72° C. for 1 minutes, which was repeated for 30 cycles, and sequencing of the obtained amplified fragment using the DNA primer P8 to confirm disfunction of the otsA gene due to introduction of frame shift mutation. The strain obtained as described above was designated as ΔOA strain.

Example 2

Construction of treY Gene-Disrupted Strain

<1> Cloning of treY Gene

Since treY gene of *Brevibacterium lactofermentum* was not known, it was obtained by using nucleotide sequences of treY genes of the other microorganisms for reference. The nucleotide sequences of treY genes were hitherto elucidated for the genera *Arthrobacter*, *Brevibacterium* and *Rhizobium* (Maruta K., et al., *Biochim. Biophys. Acta*, 1289 (1), 10–13 (1996); Genbank accession AF039919; Maruta K., et al., *Biosci. Biotechnol. Biochem.*, 60 (4), 717–720 (1996)). Therefore, referring to an amino acid sequence deduced from these nucleotide sequences, the PCR DNA primers P3 (SEQ ID NO: 14) and P4 (SEQ ID NO: 15) were synthesized first. The DNA primers P3 and P4 correspond to the regions of the nucleotide numbers of 975–992 and 2565–2584 of the nucleotide sequence of the treY gene of *Arthrobacter* species (GenBank accession D63343), respectively. Further, they correspond to the regions of the nucleotide numbers 893–910 and 2486–2505 of the treY gene of *Brevibacterium helvolum* (GenBank accession AF039919), respectively. Furthermore, they correspond to the regions of the nucleotide numbers of 862–879 and 2452–2471 of treY gene of *Rhizobium* species (GenBank accession D78001).

Then, PCR was performed by using the primers P3 and P4 and chromosomal DNA of *Brevibacterium lactofermentum* ATCC13869 as a template with a cycle consisting of reactions at 94° C. for 0.5 minute, 55° C. for 0.5 minute and 72°

C. for 2 minutes, which was repeated for 30 cycles. As a result, a substantially single kind of an amplified fragment of about 1.6 kbp was obtained. This amplified fragment was cloned into a plasmid vector pCR2.1 by using "Original TA Cloning Kit" produced by Invitrogen. Then, the nucleotide sequence was determined for about 0.6 kb.

Based on the nucleotide sequence of the partial fragment of treY gene obtained as described above, the DNA primers P16. (SEQ ID NO: 16) and P26 (SEQ ID NO: 26) were newly synthesized, and unknown regions flanking to the partial fragment was amplified by "inverse PCR" (Triglia, T. et al., *Nucleic Acids Res.*, 16, 81–86 (1988); Ochman H., et al., *Genetics*, 120, 621–623 (1988)). The chromosomal DNA of *Brevibacterium lactofermentum* ATCC 13869 was digested with a restriction enzyme BamHI, HindIII, SalI or XhoI, and self-ligated by using T4 DNA ligase (Takara Shuzo). By using this as a template and the DNA primers P16 and P26, PCR was performed with a cycle consisting of reactions at 94° C. for 0.5 minute, 55° C. for 1 minute and 72° C. for 4 minutes, which was repeated for 30 cycles. As a result, when HindIII or SalI was used as the restriction enzyme, an amplified fragment of 0.6 kbp or 1.5 kbp was obtained, respectively. The nucleotide sequences of these amplified fragments were directly determined by using the DNA primers P16 to P28 (SEQ ID NOS: 16–28). Thus, the entire nucleotide sequence of treY gene of *Brevibacterium lactofermentum* ATCC 13869 was determined as shown in SEQ ID NO: 31. The amino acid sequence encoded by this nucleotide sequence is shown in SEQ ID NOS: 31 and 32.

When homology of the sequence of the aforementioned treY gene was determined with respect to the treY gene of *Arthrobacter* sp. (GenBank accession D63343), treY gene of *Brevibacterium helvolum* (GenBank accession AF039919) and treY gene of *Rhizobium* sp. (GenBank accession D78001), the nucleotide sequence showed homologies of 52.0%, 52.3% and 51.9%, respectively, and the amino acid sequence showed homologies of 40.9%, 38.5% and 39.8%, respectively. The homologies were calculated by using software, "GENETIX-WIN" (Software Development), based on the Lipman-Person method (*Science*, 227, 1435–1441 (1985)).

<2> Preparation of Plasmid for treY Gene Disruption

In order to examine presence or absence of improvement effect in L-glutamic acid productivity by disruption of the gene coding for the enzyme in trehalose biosynthesis pathway in coryneform bacteria, a plasmid for treY gene disruption was produced. First, PCR was performed by using the primers P17 (SEQ ID NO: 17) and P25 (SEQ ID NO: 25) and the chromosomal DNA of ATCC 13869 as a template with a cycle consisting of reactions at 94° C. for 0.5 minute, 60° C. for 0.5 minute and 72° C. for 2 minutes, which was repeated for 30 cycles. The amplified fragment was digested with EcoRI and ligated to pHSG299 (Takara Shuzo) digested with EcoRI by using T4 DNA ligase (Takara Shuzo) to obtain a plasmid pHtreY. Further, this pHtreY was digested with AflII (Takara Shuzo), blunt-ended by using T4 DNA polymerase (Takara Shuzo), and self-ligated by using T4 ligase (Takara Shuzo) to construct a plasmid pHtreYA containing the treY gene having a frame shift mutation (four nucleotides were inserted after the 1145th nucleotide in the sequence of SEQ ID NO: 31) at an approximately central part thereof.

<3> Preparation of treY Gene-Disrupted Strain

By using the plasmid pCtreYA for gene disruption, a L-glutamic acid producing bacterium, *Brevibacterium lactofermentum* ATCC 13869, was transformed by the electric pulse method, and transformants were selected as to the ability to grow in CM2B medium containing 20 mg/L of kanamycin. Because the plasmid pCtreYA for treY gene disruption does not have a replication origin that could function in *Brevibacterium lactofermentum*, the transformants obtained by using the plasmid suffered recombination occurred between the trey genes on the *Brevibacterium lactofermentum* chromosome and the plasmid pCtreYA for gene disruption. From the homologous recombinant strains obtained as described above, strains in which the vector portion of the plasmid pCtreYA for gene disruption was eliminated due to re-occurrence of homologous recombination were selected based on acquired kanamycin sensitivity as a marker.

From the strains obtained as described above, a strain introduced with the desired frame shift mutation was selected. Selection of such a strain was performed by PCR using the DNA primers P19 (SEQ ID NO: 19) and P25 (SEQ ID NO: 25) with a cycle consisting of reactions at 94° C. for 0.5 minute, 55° C. for 0.5 minute and 72° C. for 1.5 minutes, which was repeated for 30 cycles, and sequencing the obtained fragment using the DNA primer P21 or P23 to confirm dysfunction of the treY gene due to introduction of frame shift mutation. The strain obtained as described above was designated as ΔTA strain.

Example 3

Evaluation of L-Glutamic Acid Producing Ability of ΔOA Strain and ΔTA Strain

The ATCC 13869 strain, ΔOA strain and ΔTA strain were each cultured for producing L-glutamic acid as follows. Each of these strains was refreshed by culturing it on a CM2B plate medium, and each refreshed strain was cultured in a medium containing 80 g of glucose, 1 g of $KH_2PO_4$, 0.4 g of $MgSO_4$, 30 g of $(NH_4)_2SO_4$, 0.01 g of $FeSO_4.7H_2O$, 0.01 g $MnSO_4.7H_2O$, 15 ml of soybean hydrolysate solution, 200 μg of thiamin hydrochloride, 3 μg of biotin and 50 g of $CaCO_3$ in 1 L of pure water (adjusted to pH 8.0 with KOH) at 31.5° C. After the culture, amount of L-glutamic acid accumulated in the medium and absorbance at 620 nm of the culture broth diluted 51 times were measured. The results are shown in Table 1.

The *Brevibacterium lactofermentum* strains of which otsA gene or treY gene was disrupted showed growth in a degree similar to that of the parent strain, and in addition, increased L-glutamic acid production compared with the parent strain.

TABLE 1

| Strain | $OD_{620}$ (×51) | L-Glutamic acid (g/L) | Yield (%) |
| --- | --- | --- | --- |
| ATCC 13869 | 0.930 | 40.2 | 48.4 |
| ΔOA | 1.063 | 43.8 | 52.8 |
| ΔTA | 0.850 | 45.6 | 54.9 |

EXPLANATION OF SEQUENCE LISTING

SEQ ID NO: 1: Primer P1 for amplification of otsA

SEQ ID NO: 2: Primer P2 for amplification of otsA

SEQ ID NO: 3: Primer P5

SEQ ID NO: 4: Primer P6

SEQ ID NO: 5: Primer P7
SEQ ID NO: 6: Primer P8
SEQ ID NO: 7: Primer P9
SEQ ID NO: 8: Primer P10
SEQ ID NO: 9: Primer P11
SEQ ID NO: 10: Primer P12
SEQ ID NO: 11: Primer P13
SEQ ID NO: 12: Primer P14
SEQ ID NO: 13: Primer P15
SEQ ID NO: 14: Primer P3 for amplification of treY
SEQ ID NO: 15: Primer P4 for amplification of treY
SEQ ID NO: 16: Primer P16
SEQ ID NO: 17: Primer P17
SEQ ID NO: 18: Primer P18
SEQ ID NO: 19: Primer P19
SEQ ID NO: 20: Primer P20
SEQ ID NO: 21: Primer P21
SEQ ID NO: 22: Primer P22
SEQ ID NO: 23: Primer P23
SEQ ID NO: 24: Primer P24
SEQ ID NO: 25: Primer P25
SEQ ID NO: 26: Primer P26
SEQ ID NO: 27: Primer P27
SEQ ID NO: 28: Primer P28
SEQ ID NO: 29: Nucleotide sequence of otsA gene
SEQ ID NO: 30: Amino acid sequence of OtsA
SEQ ID NO: 31: Nucleotide sequence of treY gene
SEQ ID NO: 32: Amino acid sequence of TreY
SEQ ID NO: 33: Primer P29
SEQ ID NO: 34: Primer P30

What is claimed is:

1. An isolated DNA coding for a protein defined in the following (A) or (B):
   (A) a protein having the amino acid sequence of SEQ ID NO: 30,
   (B) a protein having the amino acid sequence of SEQ ID NO: 30 including substitution, deletion, insertion or addition of 1–20 amino acid residues and having trehalose-6-phosphate synthase activity.

2. The isolated DNA according to claim 1, which is a DNA defined in the following (a) or (b):
   (a) a DNA comprising at least the nucleotide residues 484–4938 in the nucleotide sequence of SEQ ID NO: 29, or
   (b) a DNA which is hybridizable with a nucleotide sequence complementary to the nucleotide sequence comprising at least the nucleotide residues 484–1938 in the nucleotide sequence of SEQ ID NO: 29 under a stringent condition, and which codes for a protein having trehalose-6-phosphate synthase activity, wherein the stringent condition is 1×SSC, 0.1% SDS, at 60° C.

3. The isolated DNA according to claim 1, wherein the isolated DNA codes for a protein which has the amino acid sequence of SEQ ID NO: 30.

4. The isolated DNA according to claim 3, wherein the isolated DNA comprises at least the nucleotides 484–1938 in the nucleotide sequence of SEQ ID NO: 29.

* * * * *